United States Patent [19]

Yanagida et al.

[11] Patent Number: 5,381,792
[45] Date of Patent: Jan. 17, 1995

[54] SHOCK WAVE CURING APPARATUS CAPABLE OF CORRECTING PHASE SHIFTS CONTAINED IN ECHO SIGNALS

[75] Inventors: Yuji Yanagida; Nobuyuki Iwama; Kiyoshi Okazaki, all of Tochigi, Japan

[73] Assignee: Kabushiki Kaisha Toshiba, Kawasaki, Japan

[21] Appl. No.: 41,977

[22] Filed: Apr. 2, 1993

[30] Foreign Application Priority Data

Apr. 2, 1992 [JP] Japan ................. 4-080597

[51] Int. Cl.⁶ ............................................. A61B 17/22
[52] U.S. Cl. ................................... 128/660.03; 601/4
[58] Field of Search ......... 128/24 EL, 660.03, 660.01, 128/660.07; 601/2, 3, 4

[56] References Cited

U.S. PATENT DOCUMENTS

| | | | |
|---|---|---|---|
| 4,542,746 | 9/1985 | Takamizawa | 128/660.08 |
| 4,862,892 | 9/1989 | Green | 128/660.07 |
| 5,009,232 | 4/1991 | Hassler et al. | 128/660.03 |
| 5,065,763 | 11/1991 | Green et al. | 128/660.07 |
| 5,076,277 | 12/1991 | Iwama et al. | 128/660.03 |
| 5,105,814 | 4/1992 | Drukarey et al. | 128/660.07 |
| 5,179,954 | 1/1993 | Arima | 128/660.07 |
| 5,186,175 | 2/1993 | Hirama et al. | 128/660.07 |
| 5,215,091 | 6/1993 | Ishida | 128/24 EL |

*Primary Examiner*—K. M. Pfaffle

[57] ABSTRACT

In a shock wave generating apparatus, phase shifts contained in echo signals reflected from a calculus are corrected in order to clearly judge whether or not such a calculus is actually present at a focal point or a near region. The shock wave generating apparatus includes: a shock wave producing unit constructed of at least two transducer elements, for producing shock wave pulses used to disintegrate an object located near a focal point of said shock wave producing unit within a biological body under medical examination upon receipt of first drive pulses having first energy levels, and also for producing ultrasonic pulses used to obtain echo pulses reflected from said object near the focal point, as echo signals, upon receipt of second drive pulses having second energy levels lower than said first energy levels of the first drive pulses; an analog type phase-shift correcting unit for correcting phase shifts contained in the echo signals reflected from the object near the focal point by making respective phases of the echo signals coincident with each other as to a time domain of the analog echo signals, thereby obtaining an analog phase-corrected echo signal; a peak detecting unit for detecting a peak value of the analog phase-corrected echo signal; and a controlling unit for controlling the shock wave producing unit based on the peak value of the analog phase-corrected echo signal to determine whether or not the shock wave pulses are produced in order to destroy the object near the focal point.

20 Claims, 11 Drawing Sheets

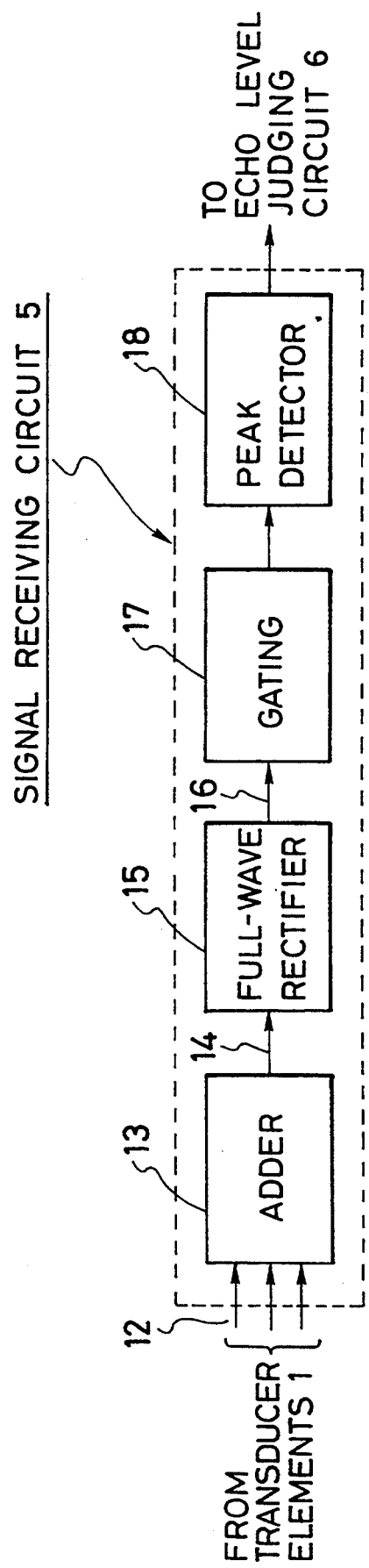

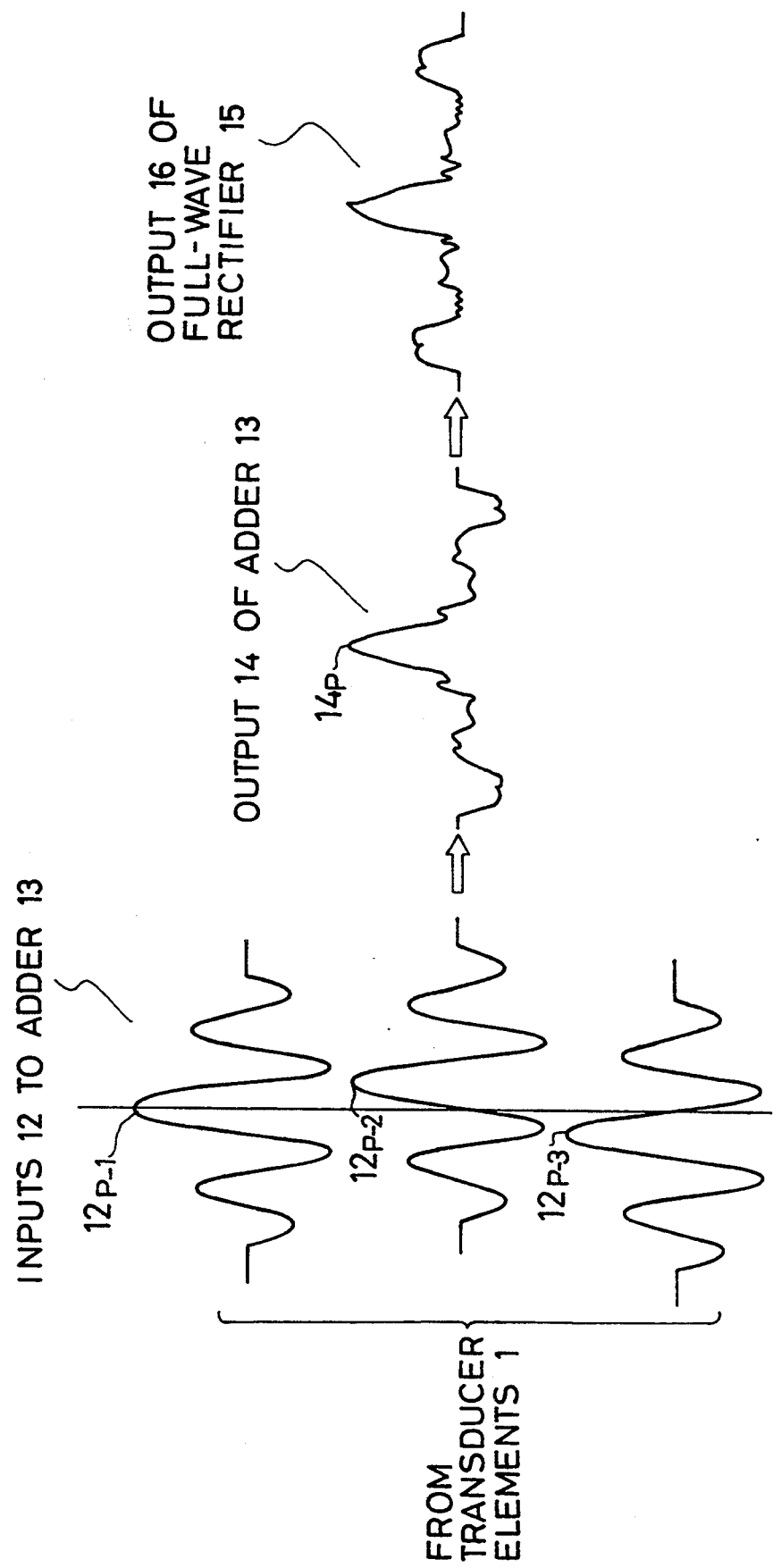

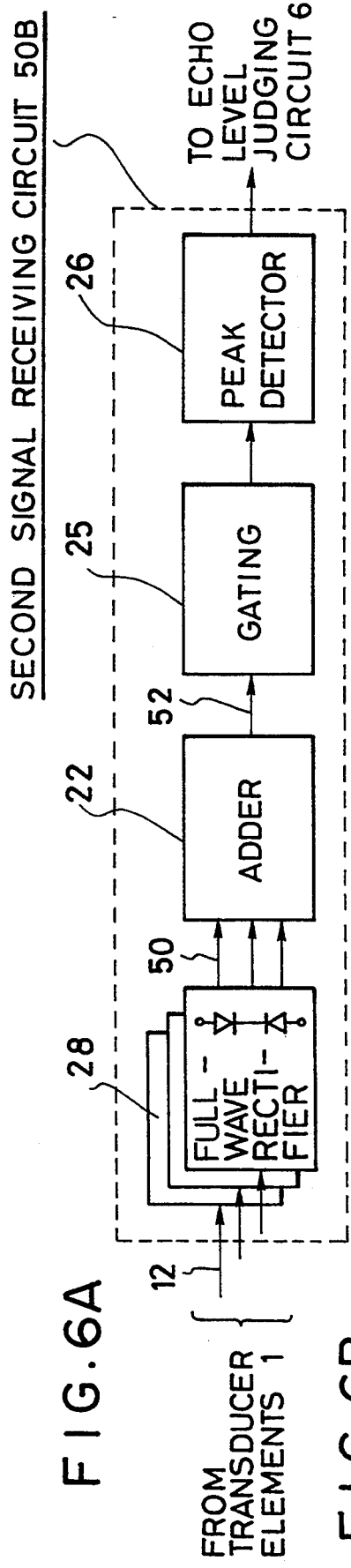
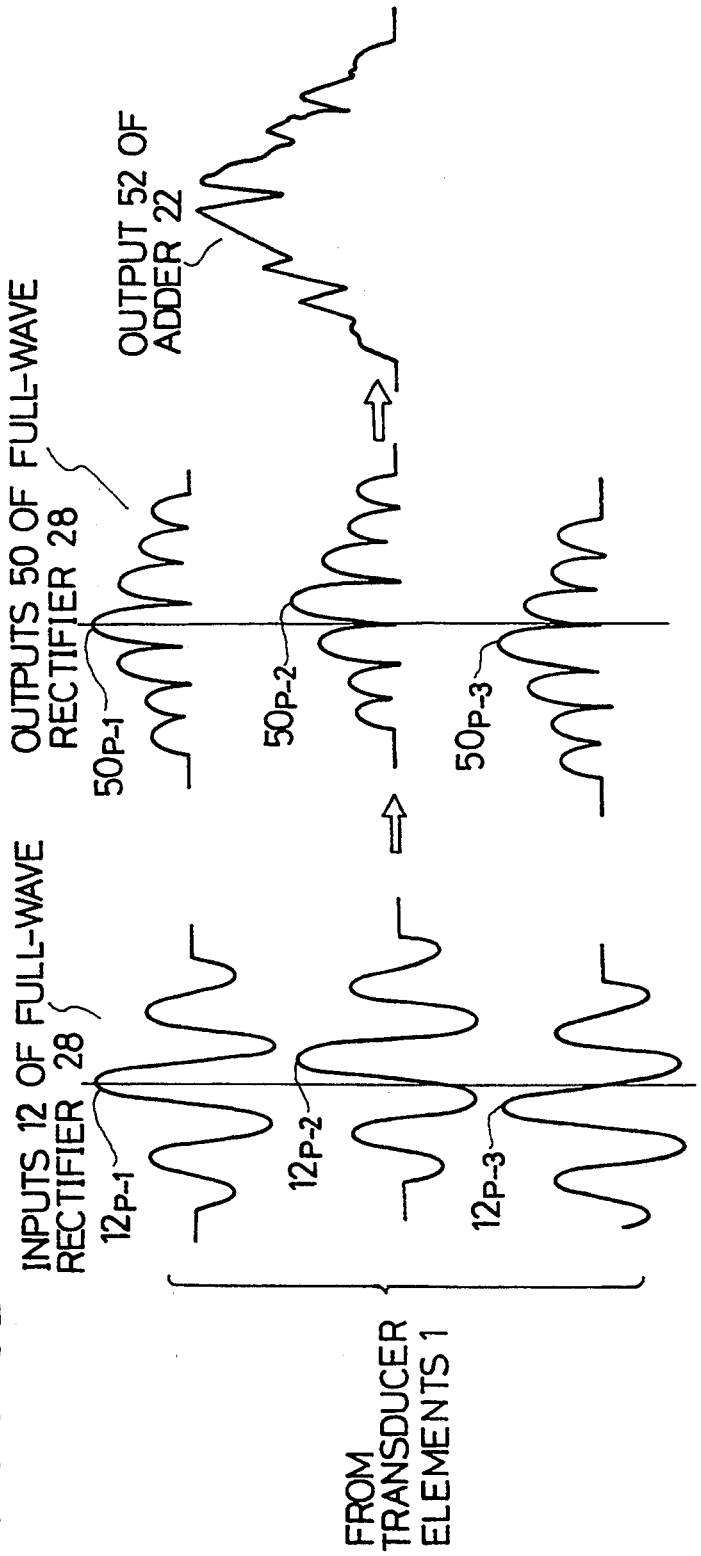

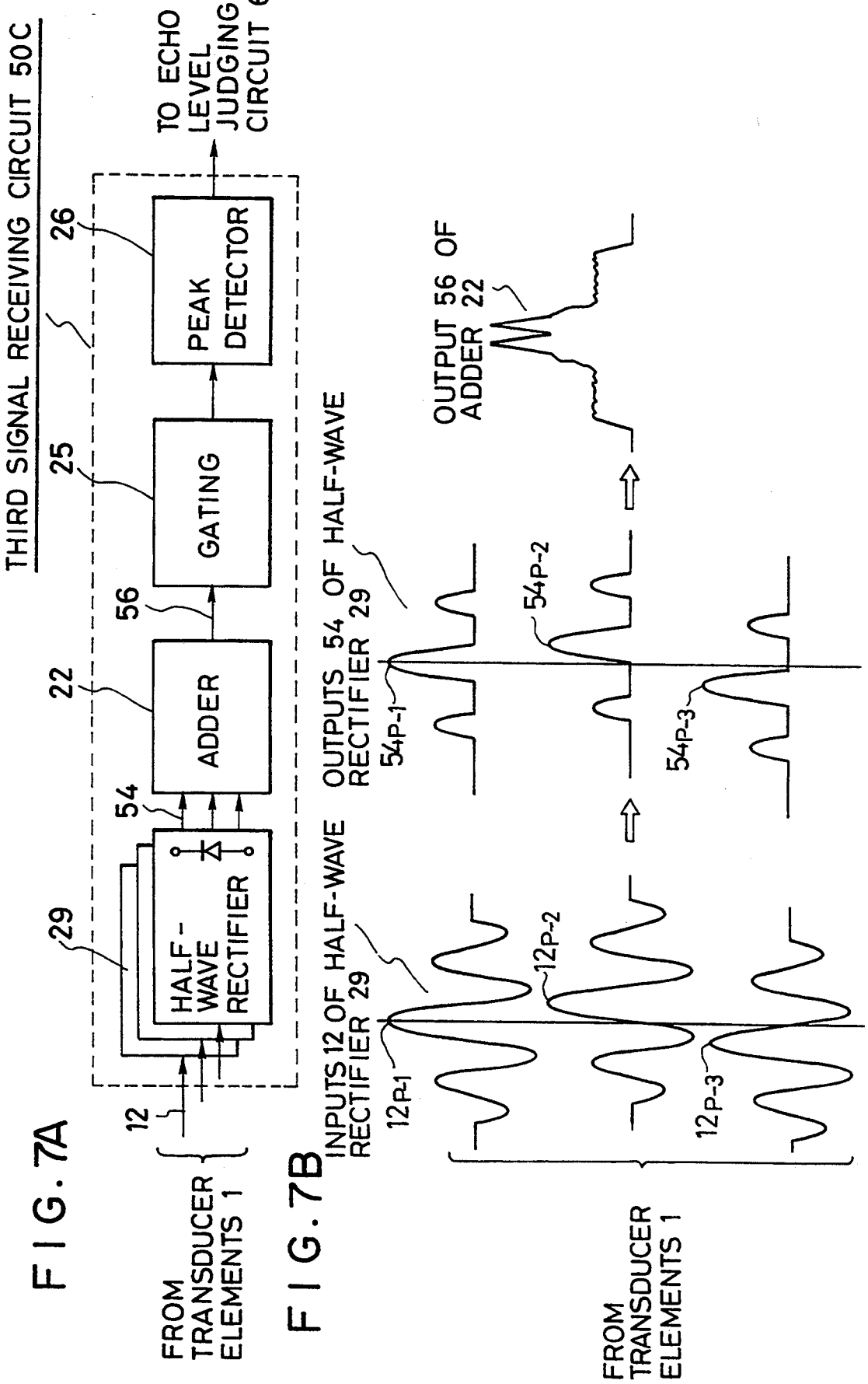

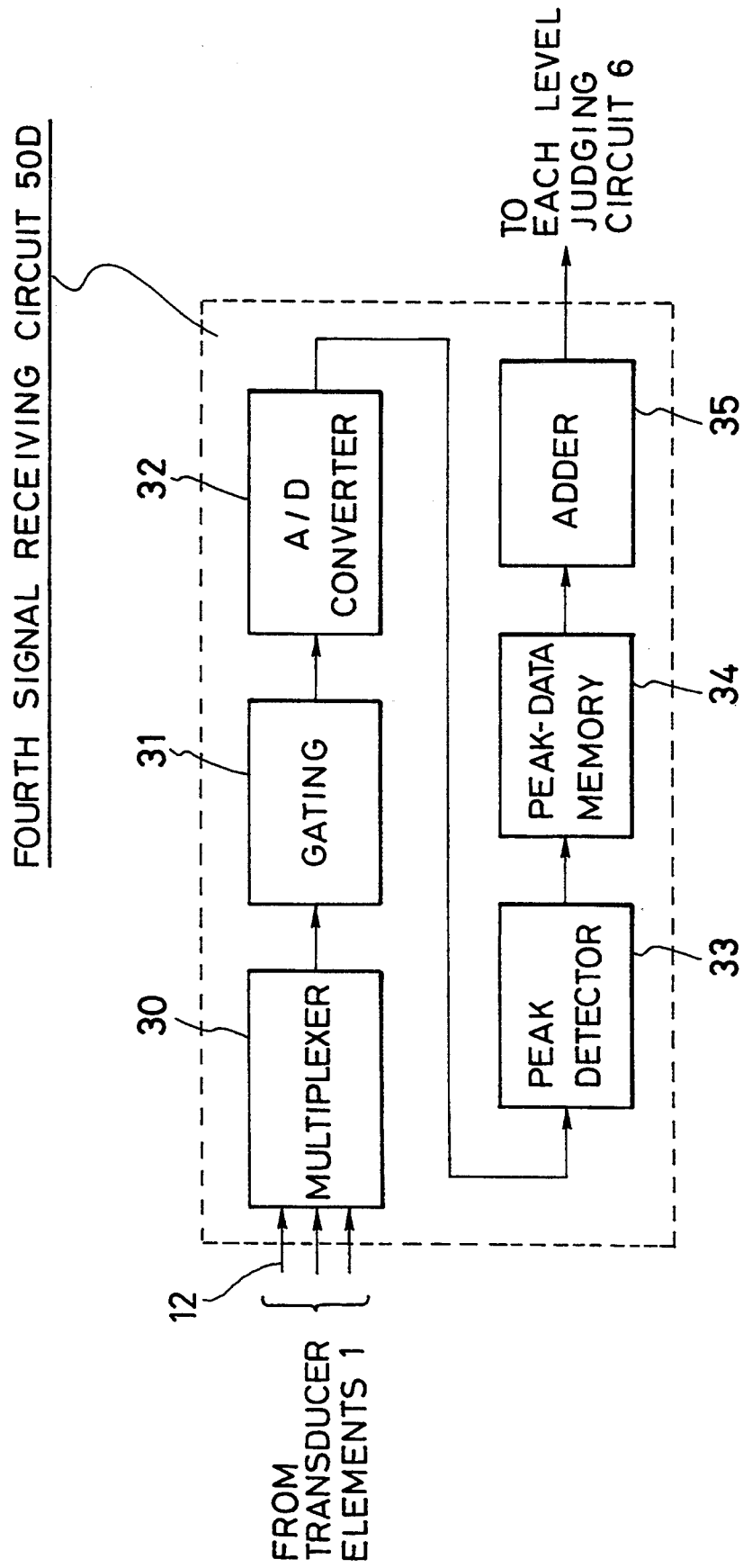

SHOCK WAVE CURING APPARATUS CAPABLE OF CORRECTING PHASE SHIFTS CONTAINED IN ECHO SIGNALS

BACKGROUND OF THE INVENTION

1. Field of the Invention

The present invention generally relates to a shock wave curing apparatus for applying shock wave pulses to a calculus to be disintegrated. More specifically, the present invention is directed to such a shock wave curing apparatus capable of correcting phase shifts contained in echo pulse signals reflected from a calculus within a biological body under medical examination by envelope-detecting these echo pulse signals.

2. Description of the Prior Art

To disintegrate, or destroy a calculus (stone) located within a biological body under medical examination, e.g., a patient, shock wave disintegrating apparatuses have been utilized and known as a "shock wave curing apparatus". In the typical shock wave curing apparatus, ultrasonic pulses having low energy are first applied to a calculus located on a focal point of a shock-wave pulse applicator before shock wave pulses produced by ultrasonic pulse having high energy are applied to destroy this calculus. As a result, since echo pulses with relatively high levels are reflected from this calculus and received by the ultrasonic pulse applicator, a decision can be made that there is a calculus to be disintegrated. Thereafter, the ultrasonic pulses with such high energy are applied to produce the shock wave pulses from the shock-wave pulse applicator. These shock wave pulses are transmitted to the calculus to be disintegrated.

Referring now to FIGS. 1, 2A, and 2B, the typical operation of the conventional shock wave curing apparatus will be explained.

In the circuit block arrangement of this conventional shock wave curing apparatus shown in FIG. 1, a shock-wave pulse applicator 1 is employed. The shock wave pulse applicator 1 is arranged by a plurality of transducer elements. This shockwave pulse applicator 1 is selectively energized by a high-voltage power source 3 and a low-voltage power source 4 via a pulser 2 in order to selectively apply shock wave pulses and ultrasonic pulses, respectively. The shock wave pulses are applied to destroy a calculus (not shown in detail) positioned at, or near a focal point of this shock wave pulse applicator 1, whereas the ultrasonic pulses are applied to check whether or not there is such a calculus by receiving ultrasonic echoes reflected from a body portion of this focal point. A sectional shape of this ultrasonic pulse applicator 1 is spherical.

When the pulser 2 is connected to the high-voltage power source 3, pulse signals having high amplitudes are produced from the pulser 2 and then supplied to the ultrasonic pulse applicator 1, so that shock waves are transmitted from this applicator 1 to the focal point area of the biological body (not shown in detail), at which the calculus is located and can be disintegrated. When the low-voltage power source 4 is connected to energize the pulser 2, ultrasonic pulses are transmitted from this shockwave pulse applicator 1 to this focal point area. As a result, there is such a calculus to be destroyed in this focal point area, echo pulses with relatively high levels are reflected from this calculus and received by this applicator 1 to produce echo signals with high signal levels.

The resultant echo signals are supplied to a signal receiving circuit 5. In this signal receiving circuit 5, these echo signals are first summed with each other by an adder 13 (see FIG. 2A). The added echo signal 14 is rectified by a full-wave rectifier 15. Thereafter, the rectified echo signal is processed in a gating circuit 17 and a peak detector 18 to obtain a peak level of the echo signals (see FIG. 2A).

The peak level of the echo signals is compared with a threshold level derived from a threshold level setting circuit 9 in an echo level judging circuit 6. Then, if the echo signals are received from the calculus, the resultant peak level of the echo signals becomes higher than the threshold level, so that the echo level judging circuit 6 judges that the calculus to be disintegrated is located at, or near this focal point of the shockwave pulse applicator 1. Accordingly, the high-voltage power source 3 is connected to the pulser 2 so as to transmit shock waves from the applicator 1 to this calculus, whereby this calculus can be destroyed.

In FIG. 1, an ultrasonic probe 10 is employed to scan the biological body under control of an ultrasonic imaging apparatus 11, so that a B-mode image of this scanned biological body is displayed on a TV monitor 8. An image of the above calculus may be displayed together with this B-mode image.

Various drawbacks of this conventional shock wave curing apparatus shown in FIG. 1 will now be explained with reference to FIGS. 2A and 2B.

FIG. 2A shows an internal circuit arrangement of the signal receiving circuit 5, and FIG. 2B illustrates waveforms of the echo signals.

That is, as shown in FIG. 2B, the echo signals 12 derived from the shock wave applicator 1 own phase shifts with each other with respect to a time domain of the echo signals. As a result of these phase shifts, the output signal 14 of the adder 13 has relatively low peak. In other words, as illustrated in FIG. 2B, since three peaks 12p-1, 12p-2, 12p-3 of these echo signals 12 are not coincident with each other at a time instant "$t_1$", the level of the single peak "14p" does not become three times higher than the respective peaks 12p-1, 12p-2, 12p-3 of the echo signals 12. As a consequence, the output 16 of the full-wave rectifier 15 has a relatively low peak level.

Thus, the resultant echo level of the peak detector 18 does not become so high, as compared with the threshold level. In the worst case, there are some risks that the echo level judging circuit 6 would mistakenly judge "no calculus" even if a calculus is actually present at or near the focal point within the biological body. Furthermore, the special resolution of the conventional shock wave curing apparatus is lowered.

SUMMARY OF THE INVENTION

The present invention has been made in an attempt to solve the above-described drawbacks, and therefore, has an object to provide a shock wave curing apparatus capable of correcting phase shifts contained in echo signals derived from a shockwave pulse applicator.

Another object of the present invention is to provide a shock wave curing apparatus capable of correcting such phase shifts by employing a simple circuit arrangement.

A further object of the present invention is to provide a shock wave curing apparatus capable of correcting phase shifts of echo signals in a digital correction manner.

To achieve these objects, a shock wave curing apparatus, according to one aspect of the present invention, comprises:

shock wave producing means (1:2:3:4) constructed of at least two transducer elements, for producing shock wave pulses used to disintegrate an object located near a focal point of said shock wave producing means within a biological body under medical examination upon receipt of first drive pulses having first energy levels, and also for producing ultrasonic pulses used to obtain echo pulses reflected from said object near the focal point, as echo signals, upon receipt of second drive pulses having second energy levels lower than said first energy levels of said first drive pulses;

analog type phase-shift correcting means (20:22:28:29) for correcting phase shifts contained in said echo signals reflected from the object near the focal point by making respective phases of said echo signals coincident with each other as to a time domain of said analog echo signals, thereby obtaining an analog phase-corrected echo signal (24:52:56);

peak detecting means (26) for detecting a peak value of said analog phase-corrected echo signal (24:52:56); and controlling means (6:9) for controlling said shock wave producing means (1:2:3:4) based on said peak value of the analog phase-corrected echo signal (24:25:56) as to determine whether or not said shock wave pulses are produced in order to destroy the object near the focal point.

According to another aspect of the present invention, a shock wave curing apparatus comprises:

shock wave producing means (1:2:3:4) constructed of at least two transducer elements, for producing shock wave pulses used to disintegrate an object located near a focal point of said shock wave producing means within a biological body under medical examination upon receipt of first drive pulses having first energy levels, and also for producing ultrasonic pulses used to obtain echo pulses reflected from said object near the focal point, as analog echo signals, upon receipt of second drive pulses having second energy levels lower than said first energy levels of the first drive pulses;

digital type phase-shift correcting means (30:32) for correcting phase shifts contained in said echo signals reflected from the object near the focal point by converting said analog echo signals into digital echo signals, thereby obtaining digital phase-corrected echo signals with respect to a time domain of said echo signals;

peak detecting means (33) for detecting peak values of said digital phase-corrected echo signals; and controlling means (6:9) for controlling shock wave producing means (1:2:3:4) based on said peak values of the digital phase-corrected echo signals so as to determine whether or not said shock wave pulses are produced in order to destroy the object near the focal point.

BRIEF DESCRIPTION OF THE DRAWINGS

For a better understanding of the present invention, reference is made of the following detailed description with reference to the accompanying drawings, in which:

FIG. 2A is a schematic block diagram of an internal circuit of the signal receiving circuit 5 shown in FIG. 1;

FIG. 2B schematically shows waveforms of echo signals appearing in the circuit portions of the signal receiving circuit 5;

FIG. 6A is a schematic block diagram of a internal circuit of a second signal receiving circuit 50B employed in another shock wave curing apparatus according to a second preferred embodiment of the present invention;

FIG. 6B schematically represents waveforms of echo signals appearing in the second signal receiving circuit 50B;

FIG. 7A is a schematic block diagram of a third signal receiving circuit 50C employed in another shock wave curing apparatus according to a third preferred embodiment of the present invention;

FIG. 7B schematically shows waveforms of echo signals appearing in the third signal receiving circuit 50C;

FIG. 8 is a schematic block diagram of an internal circuit of a fourth signal receiving circuit 50D employed in a shock wave curing apparatus according to a fourth preferred embodiment of the present invention;

DETAILED DESCRIPTION OF THE PREFERRED EMBODIMENTS

ARRANGEMENT OF FIRST SHOCK WAVE CURING APPARATUS

Figure 3:
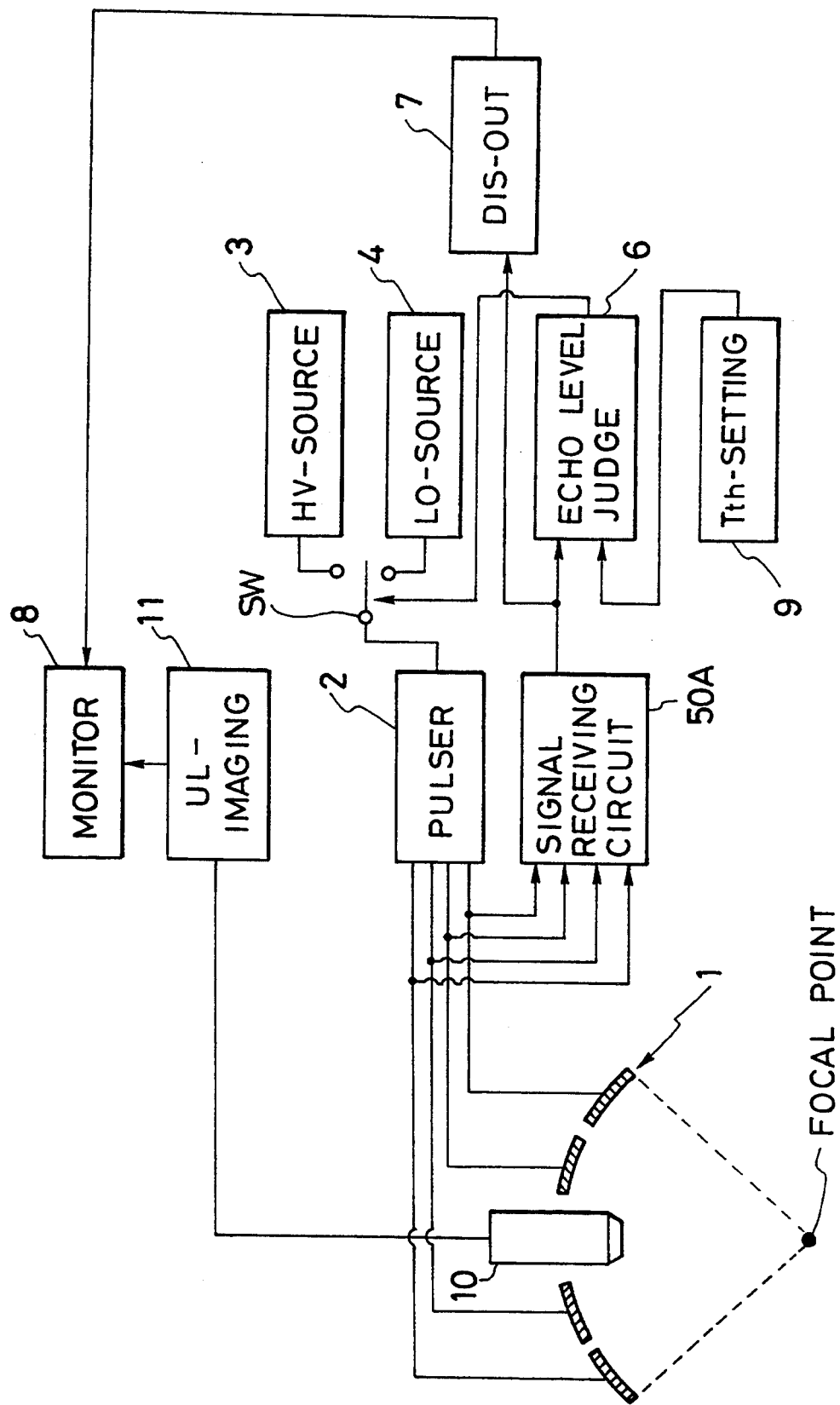
FIG. 3 schematically shows an overall arrangement of a shock wave curing apparatus according to a first preferred embodiment of the present invention.
Figure 4:
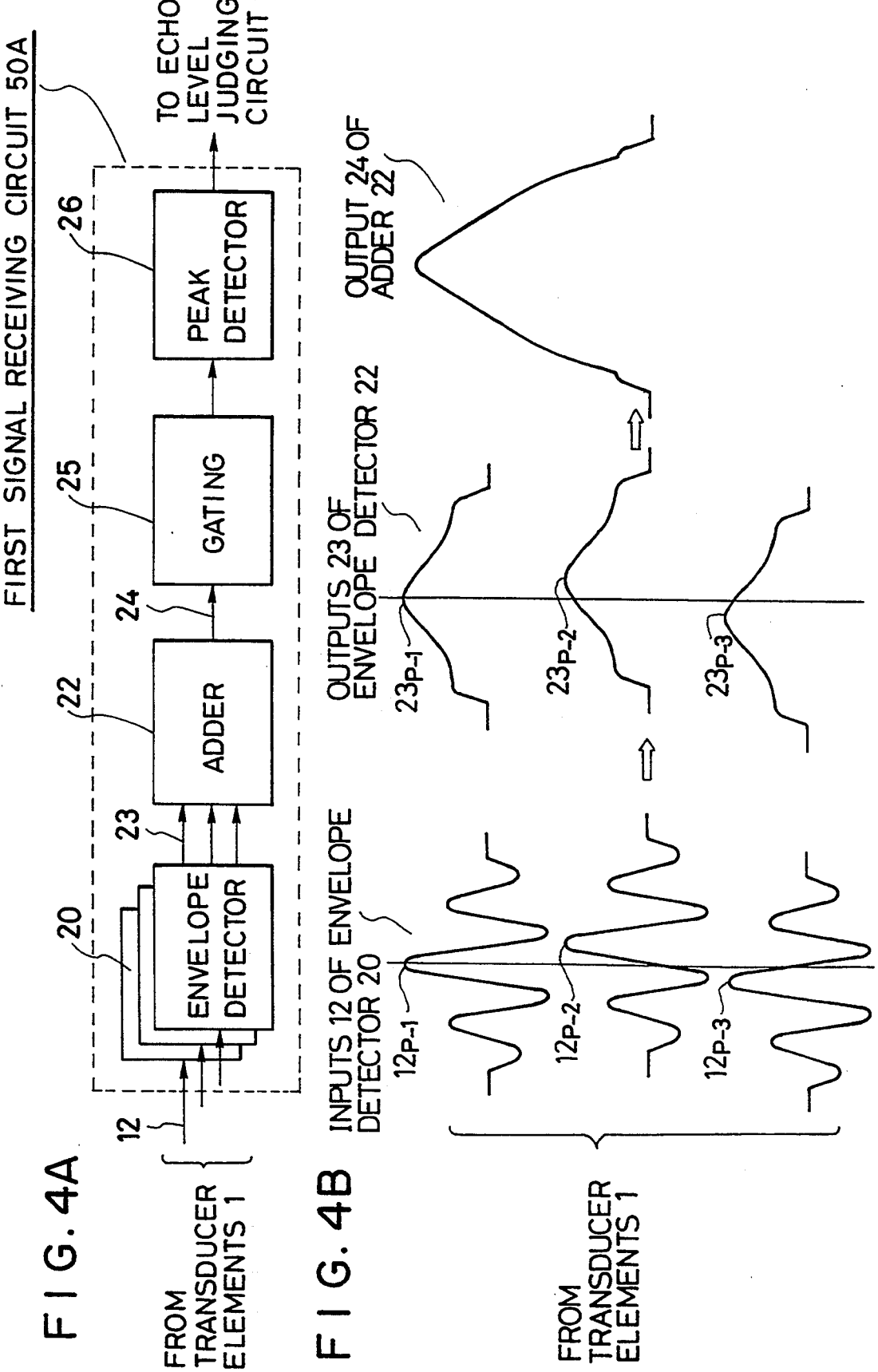
FIG. 4A is a schematic block diagram of an internal circuit of the first signal receiving circuit 50A employed in the first shock wave curing apparatus of FIG. 3.
FIG. 4B schematically illustrates waveforms of echo signals appearing in the first signal receiving circuit 50A.
Figure 5:
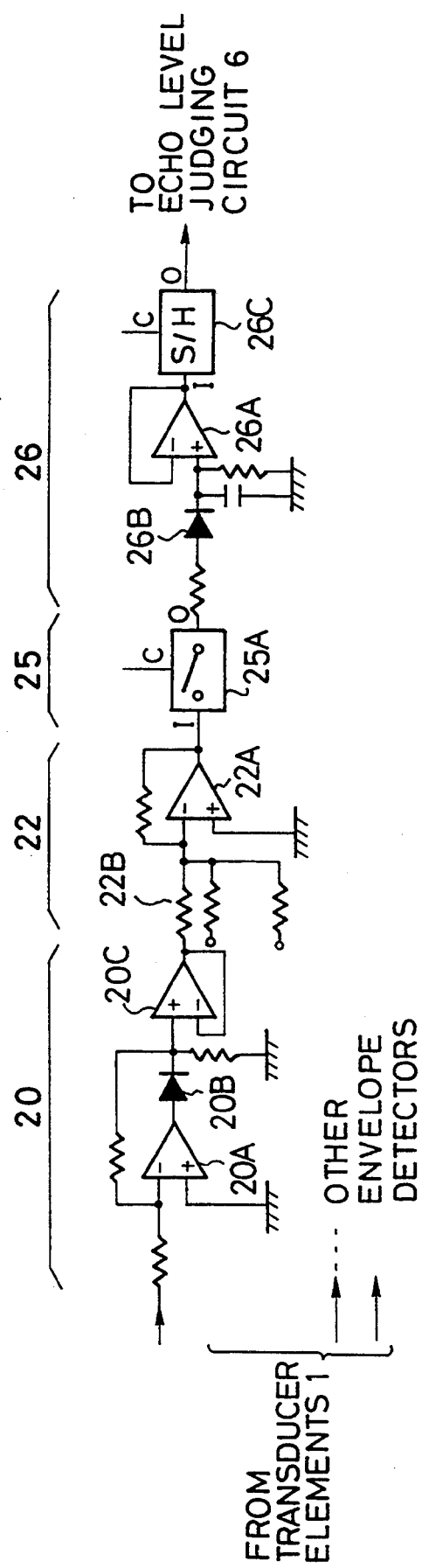
FIG. 5 shows a practical circuit diagram of the first signal receiving circuit 50A.

FIG. 3 schematically shows an overall circuit arrangement of a shock wave curing apparatus according to a first preferred embodiment. FIG. 4A schematically represents an internal circuit arrangement of a first signal receiving circuit 50A employed in the first shock wave curing apparatus of FIG. 3, and FIG. 4B indicates waveforms of echo signals appearing in the first signal receiving circuit 50A. FIG. 5 is an actual circuit arrangement of the first signal receiving circuit 50A.

Figure 1:
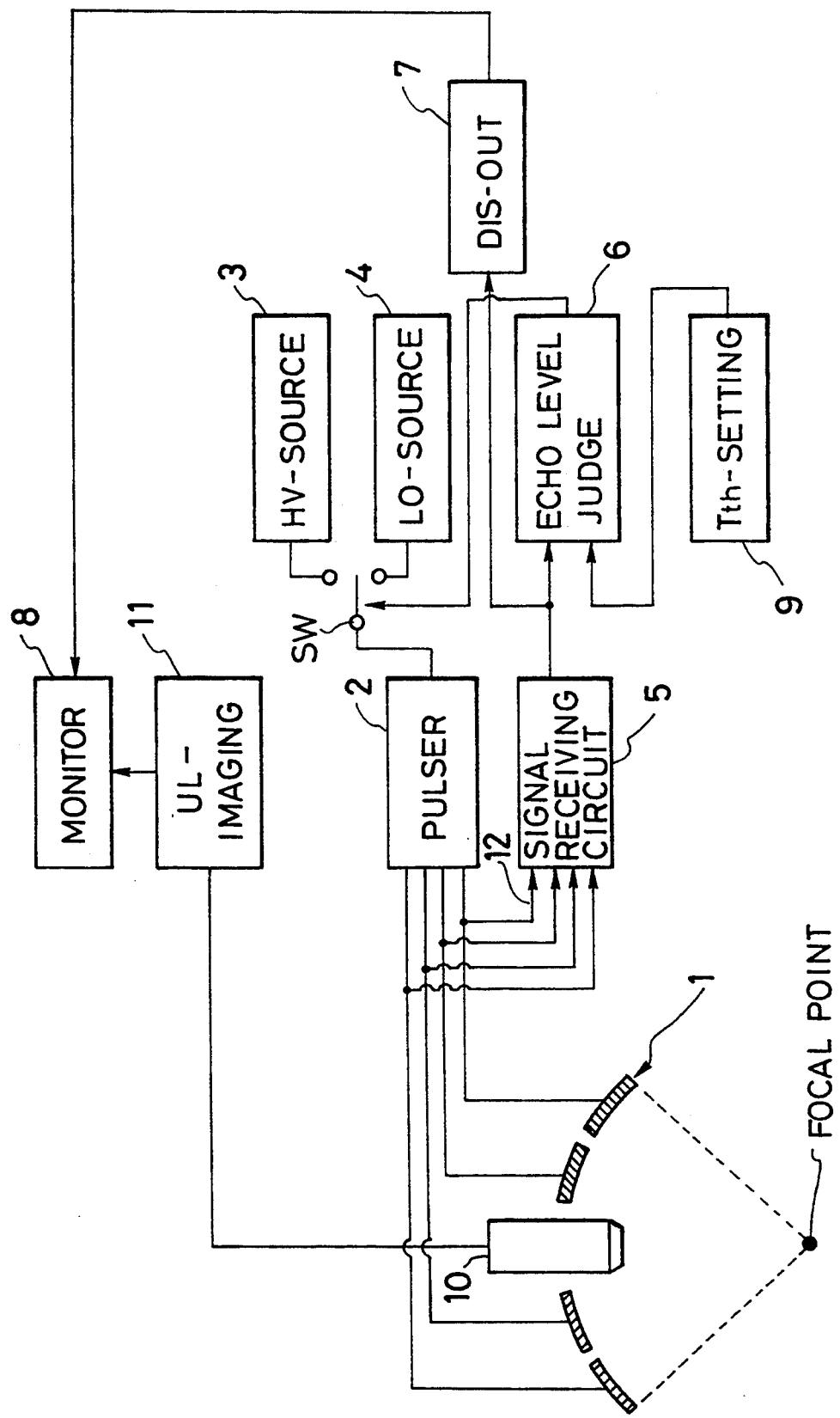
FIG. 1 is a schematic block diagram for showing an arrangement of the conventional shock wave curing apparatus.

As easily seen from the overall circuit arrangement of the first shock wave curing apparatus shown in FIG. 3, most of the circuit arrangement thereof is similar to that of the conventional shock wave curing apparatus indicated in FIG. 1. Accordingly, only the different circuit will now be explained in detail. A major featured circuit of this first shock wave curing apparatus is a first signal receiving circuit 50A as shown in FIG. 4A.

As indicated in FIG. 4A, the first signal receiving circuit 50A is arranged by envelope detectors 20, an adder 22, a gating circuit 25, and a peak detector 26. These circuit elements 20, 22, 25, 26 are connected in a series form. The number of envelope detectors 20 is coincident with the quantity of transducer elements of the shock wave pulse applicator 1. Normally speaking, at least two sets of transducer elements 1 are employed, and arranged in a spherical form, as viewed in a sectional direction. Accordingly, three sets of transducer elements 1 are employed in the first shock wave curing apparatus.

For the sake of simplicity, only three envelope detectors 20 are shown in FIG. 4A.

In the internal circuit arrangement of the first signal receiving circuit 50A, the echo signals 12 derived from the respective transducer elements of the shock wave pulse applicator 1 are first envelope-detected by the respective envelope detectors 20. The envelope-detected echo signals 23 are summed, or added with each other in the adder 22 to obtain an added echo signal 24. Thereafter, the added echo signal 24 is supplied to the gating circuit 25 in order to gate only the echo signal derived directly from the focal point and also from an adjoining portion thereof. The gated echo signal is further supplied to the peak detector 26 so as to detect a peak value (level) thereof. This peak value will then be supplied to the echo level judging circuit 6 as an echo level signal indicative of a reflection echo strength around the focal point.

OVERALL OPERATION OF FIRST SHOCK WAVE CURING APPARATUS

Referring now to FIG. 3 and to FIG. 4B, an overall operation of the first shock wave curing apparatus will be described. As previously explained, since the shock wave pulse applicator 1 is driven via the pulser 2 by the low-voltage power source 4, the checking ultrasonic wave pulses are transmitted from the three transducer elements 1 toward the focal point within the biological body (not shown in detail) under medical examination. Assuming now that a calculus (not shown either) is located at, or near this focal point, these checking ultrasonic pulses are reflected as echo pulses from not only a tissue of the biological body, but also this calculus.

As a result, the echo pulses are received and converted into the echo signals 12 by the transducer elements 1, as indicated in FIG. 4B. It should be noted that as explained in FIG. 2B, these three echo signals 12 have different peak amplitudes 12p-1, 12p-2, 12p-3 with respect to the time instant "$t_1$". These echo signals 12 are firstly envelope-detected by the respective envelope detectors 20 to obtain the envelope-detected echo signals 23, as indicated in FIG. 4B. These envelope-detected echo signals 23 still own different peak amplitudes 23p-1, 23p-2, 23p-3 with respect to the time instant "$t_1$". However, when these envelope-detected echo signals 23 are supplied to the adder 22, these echo signals 23 are added to each other with equalizing the time axis thereof (see waveform 24 of FIG. 4B).

A major feature of this first signal receiving circuit 50A will now be explained more in detail. Since the surface shape of the calculus is complicated, the echo signals 12 reflected therefrom own such different peak amplitudes 12p-1, 12p-2, 12p-3 with respect to the time domain. However, according to the major feature of this first signal receiving circuit 50A, the envelope-detected echo signals 23 contain only positive (or negative) components as clearly indicated by FIG. 4B, so that these signal components are not cancelled with each other while these envelope-detected echo signals 23 are added to each other in the adder 22. In other words, the respective peak amplitudes 23p-1, 23p-2, 23p-3 of the envelope-detected echo signals 23 are added with each other in a positive manner. As a consequence, since no interference is made in these envelope-detected echo signals 23, such a high reflection-echo intensity of the added echo signal 24 can be detected by the peak detector 26, as represented in FIG. 4B.

Referring back to FIG. 3, this peak echo level of the echo signal 24 detected by the peak detector 26 is supplied to echo-level judging circuit 6. In this echo-level judging circuit 6, the peak echo level of the echo signal 24 is compared with the threshold level "Tth" derived from the threshold level setting circuit 9. Then, when the peak echo level is higher than the threshold level "Tth", this echo-level judging circuit 6 judges that the calculus is located at, or near the focal point of the shock wave pulse applicator 1. Accordingly, the echo-level judging circuit 6 furnishes a switching signal to the selecting switch "SW", so that the low-voltage power source is changed into the high-voltage power source 3 to be connected to the pulser 2. Thus, since the shock wave pulse applicator 1 is driven by the high-voltage power source 3, the shock wave pulses are transmitted toward the focal point so as to destroy the calculus detected by the first signal receiving circuit 50A employed in the first shock wave curing apparatus.

On the other hand, since the output signal of this first signal receiving circuit 50A is supplied via the display output circuit 7 to the TV monitor 8 and also the ultrasonic imaging probe 10 is operated under control of the ultrasonic imaging unit 11, an image of this calculus can be displayed together with the B-mode image on the TV monitor 8. As a consequence, presence of this calculus to be disintegrated can be observed, while performing the shock wave curing operation.

PRACTICAL CIRCUIT ARRANGEMENT OF FIRST SIGNAL RECEIVING CIRCUIT 50A

Referring now to FIG. 5, a practical circuit diagram of the above-explained first signal receiving circuit 50A will be summarized.

In FIG. 5, a single envelope detector 20 is arranged by an operational amplifier 20A, a diode 20B, and a buffer amplifier 20C. The adder 22 is constructed of an operational amplifier 22A with three input resistors 22B. The gating circuit 25 is realized by a semiconductor switch 25A. Then, the peak detector 26 includes an operational amplifier 26A with an input diode circuit 26B, and a sample/hold circuit 26C.

Since all of these practical circuit configurations per se are known in the art, no further detailed explanation thereof is made in the specification.

SECOND SIGNAL RECEIVING CIRCUIT 50B

FIG. 6A is a schematic block diagram of a second signal receiving circuit 50B employed in a shock wave curing apparatus according to a second preferred embodiment of the present invention, and FIG. 6B represents waveforms of echo signals appearing in the second signal receiving circuit 50B.

It should be understood that since the second shock wave curing apparatus may be arranged by merely substituting the first signal receiving circuit 50A of FIG. 4A by the second signal receiving circuit 50B of FIG. 6A, no entire circuit arrangement of this second shock wave curing apparatus is shown. Similarly, overall circuit arrangements of the subsequent shock wave curing apparatuses are not illustrated, but only the relevant signal receiving circuits will be shown and described with reference to waveform charts.

In the second signal receiving circuit 50B of FIG. 6A, full-wave rectifies 28 are newly employed instead of the above-described envelope detectors 20 employed in the first signal receiving circuit 50A. The remaining circuit arrangement of the second signal receiving circuit 50B is identical to that of the first signal receiving circuit 50A.

Assuming now that three echo signals 12 having three different peak amplitudes 12p-1, 12p-2, 12p-3 with respect to the time instant "$t_1$" (see FIG. 6B) are supplied to the respective full-wave rectifiers 28, full-wave-rectified echo signals 50 are obtained from the outputs of the fullwave rectifiers 28. Although these rectified echo signals 50 still owns different peak amplitudes 50p-1, 50p-2, 50p-3 with respect to the time domain, since these signals 50 contain positive signal components, no signal component cancellation occurs even if these echo signals 50 are added to each other in the adder 22. As a consequence, an output signal 52 of this adder 22 can have a high peak amplitude, as compared with that of the conventional echo signal 16 (see FIG. 2B).

In accordance with the second signal receiving circuit 50B, there is a merit of a simpler circuit arrangement than that of the first signal receiving circuit 50A.

THIRD SIGNAL RECEIVING CIRCUIT 50C

FIG. 7A is a schematic block diagram of a third signal receiving circuit 50C employed in a shock wave curing apparatus according to a third preferred embodiment of the present invention, and FIG. 7B shows waveforms of echo signals appearing in this third signal receiving circuit 50C.

In the third signal receiving circuit 50C of FIG. 7A, half-wave rectifiers 29 are newly employed instead of the full-wave rectifier 28 shown in the second signal receiving circuit 50B.

When the echo signals 12 having the different peak amplitudes 12p-1, 12p-2, 12p-3 are inputted to the respective half-wave rectifiers 29, half-wave-rectified echo signals 54 are outputted from the half-wave rectifiers 29. These rectified echo signals 54 have different peak amplitudes 54p-1, 54p-2, 54p-3 with regard to the time domain. Eventually, since these rectified echo signals 54 contain only positive components, the phase shifts among these peak signal levels can be corrected by adding these echo signals 54 to each other in the adder 22, and thus, an echo signal 56 outputted from the adder 22 can still have a higher peak amplitude than that of the conventional echo signal 16.

As apparent from the foregoing description, a more simple circuit arrangement of the third signal receiving circuit 50C can be realized, as compared with the first and second signal receiving circuits 50A and 50B.

ARRANGEMENT OF FOURTH SIGNAL RECEIVING CIRCUIT 50D

In the above-described first to third signal receiving circuits 50A, 50B and 50C, the phase shift corrections for the echo signals with different peak amplitudes have been performed by way of the analog signal processing manners.

Alternatively, according to the present invention, such phase shift corrections may be carried out by way of digital signal processing manners.

That is, a fourth signal receiving circuit 50D executes such a digital phase shift correction, which will be described in detail.

FIG. 8 is a schematic circuit diagram of this fourth signal receiving circuit 50D. The fourth signal receiving circuit 50D includes a multiplexer 30 for acquiring the echo signals 12 from the shock wave pulse applicator 1 and for sequentially outputting the echo signals 12 to a gating circuit 31. The gating circuit 31 gates only the echo signals reflected from the focal point and the region near this focal point. The gated echo signals are A/D-converted by an A/D converter 32 into digital echo signals. The resultant digital echo signals are processed in a peak detector 33 in such a manner that peak values contained in these digital echo signals are detected. The detected digital peak values are then stored into a peak-data memory 34. Subsequently, all of these peak data are added to each other by an adder 35, thereby obtaining a digital peak level of the echo signals 12.

Then, this digital peak level of the echo signal 12 derived from the adder 35 is compared with the threshold level "Tth" of the threshold level setting circuit 9 in the echo level judging circuit 6 in order to judge whether or not the calculus is located within the region of the biological body at or near the focal point in a similar manner to those of the first to third shock wave curing apparatuses shown in FIGS. 3 to 7.

In accordance with the fourth signal receiving circuit 50D employed in the fourth shock wave curing apparatus shown in FIG. 8, since the peak values of the inputted echo signals 12 are added to each other as the digital signal form, the phase components of these echo signals 12 are completely neglected, so that the phase shifts of the peak amplitudes of these echo signals can be corrected, and thus the echo levels of the echo signals are not lowered.

PRACTICAL CIRCUIT OF FOURTH SIGNAL RECEIVING CIRCUIT 50D

Figure 9:
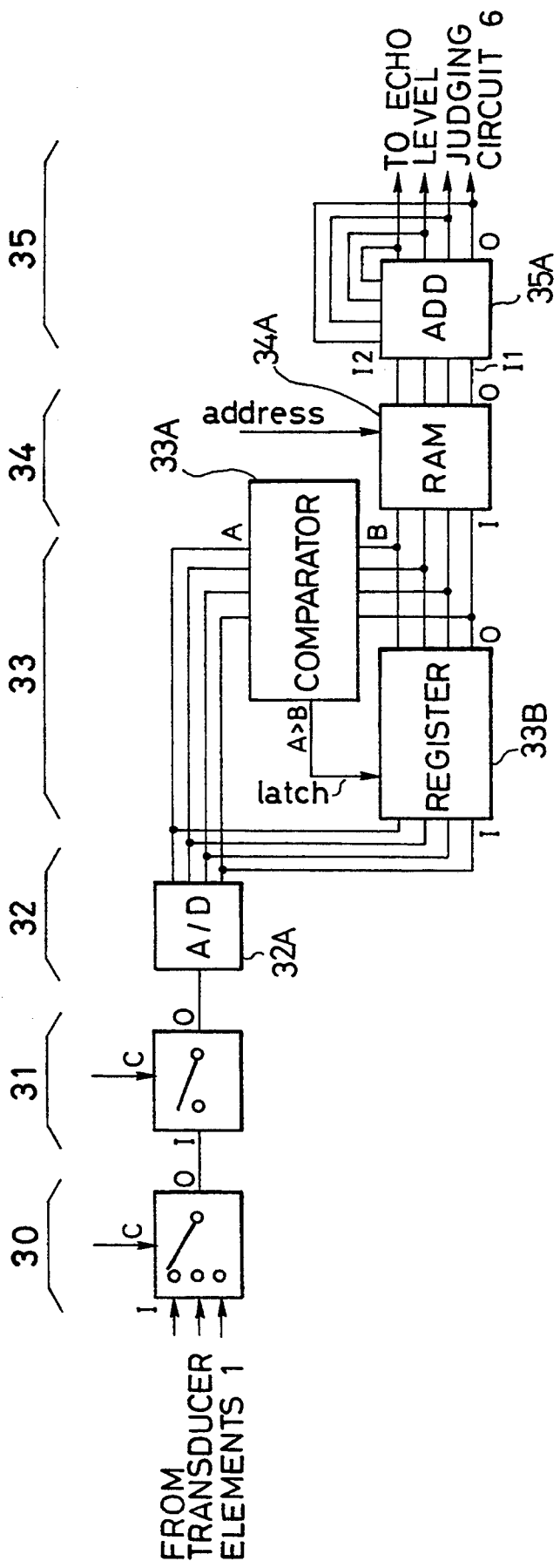
FIG. 9 is a practical circuit diagram of the fourth signal receiving circuit 50D.

FIG. 9 shows an actual circuit diagram of the fourth signal receiving circuit 50D. Since the circuit elements of this practical signal receiving circuit 50D are well known in the art, only a specific circuit arrangement thereof will be explained.

The peak detector 33 is arranged by a comparator 33A and a register 33B. This register 33B temporarily stores the digital echo signals derived from the A/D converter 32A. The amplitude level values of these digital echo signals are compared with each other so as to detect the digital peak values. When the digital peak values are detected (A>B shown in FIG. 9), a latch signal is supplied from the comparator 33A to the register 33B.

Thereafter, only the peak value data outputted from the register 33B are stored in a RAM 34A. Then, these peak value data are sequentially read out from the RAM 34A and added to each other in an adder 35A. Finally, the desirable echo peak level is obtained from the adder 35A.

MODIFICATIONS

As apparent from the foregoing descriptions, the present invention is not limited to the above-explained preferred embodiments, but also may be changed, substituted, or modified without departing from the technical spirit and scope of the invention.

Figure 10:
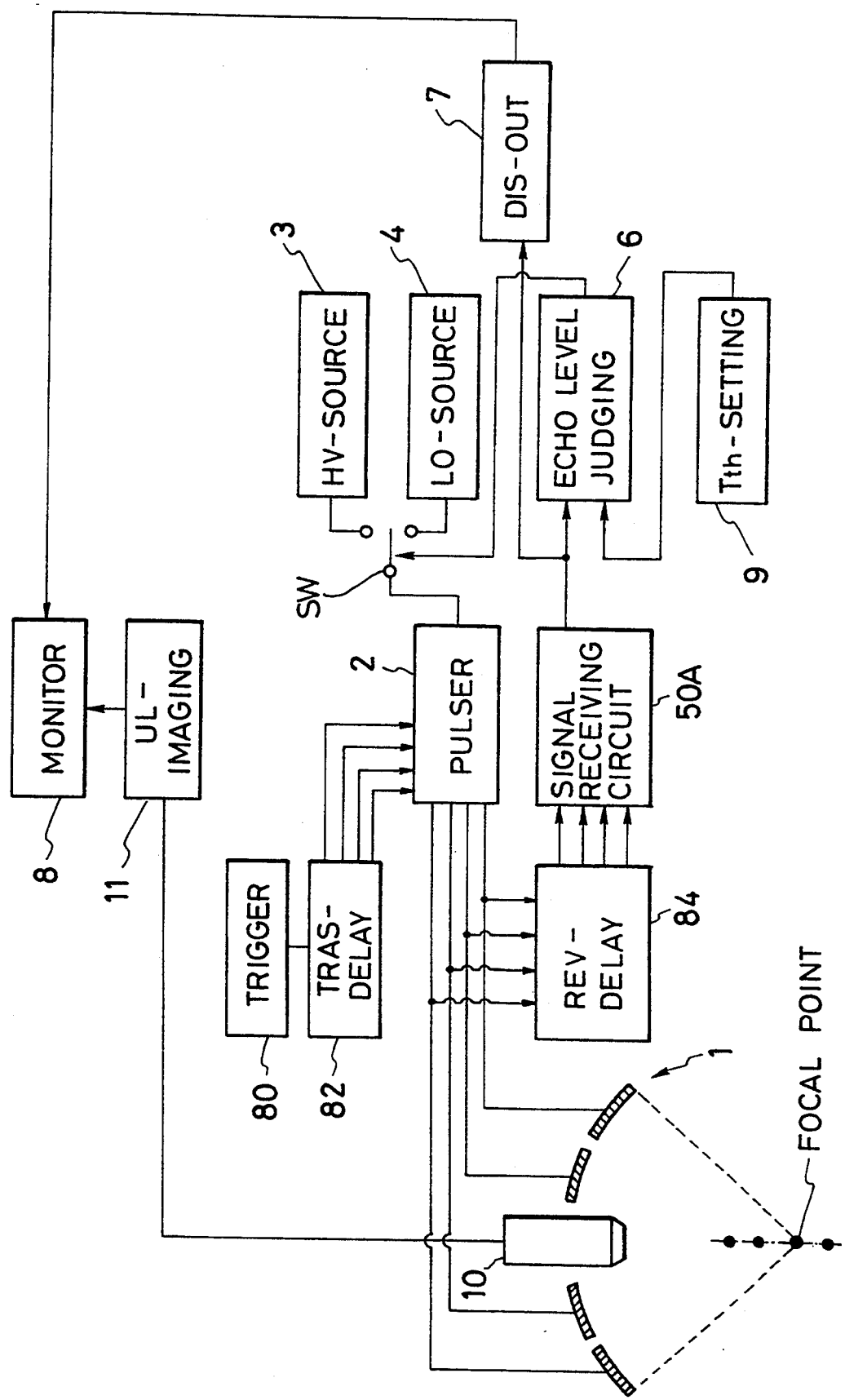
FIG. 10 schematically indicates an overall circuit arrangement of an electronic focusing type shock wave curing apparatus according to a further preferred embodiment of the present invention.

For instance, FIG. 10 shows an overall arrangement of another shock wave curing apparatus, according to the present invention, which can perform a so-called "electronic focusing" in the transducer elements. That is, in the electronic focusing type shock wave curing apparatus, a trigger circuit 80 and a transmitter delay circuit 82 are newly employed to be connected with the pulser 2, and similarly a receiver delay circuit 84 is newly employed to be connected to the first signal receiving circuit 50A. Thus, preselected delay times are given to the pulser 2, so that the ultrasonic pulses are produced at different timings from the transducer elements 1. Then, the electronic focusing control can be carried out to vary the focal points, as shown in FIG. 10. It should be noted that such delay times opposite to those of the transmission should be applied to the respective echo signals obtained from the transducer elements 1 in the receiver delay circuit 84. That is, the delay times given to the respective channels during the transmission of the ultrasonic pulses are completely reversed to those given to the respective channels during the reception of the echo signals in order that the same focal point can be formed during both of the transmission and reception operations. Since the electronic focusing control is employed, the shape of the transducer elements 1 is no longer made spherical, many other shapes thereof may be utilized such as a plane shape.

Moreover, instead of the first signal receiving circuit 50A, other signal receiving circuits 50B, 50C, 50D may be employed in this electronic focusing type shock wave curing apparatus of FIG. 10.

An acoustic lens may be employed instead of the electronic focus control circuit arrangement 80, 82, 84.

At least two sets of ring-shaped transducer elements may be employed instead of the spherical-shaped transducer elements 1. Furthermore, a large number of transducer elements are arranged in the spherical shape, as viewed in a sectional plane thereof, and may be selectively driven by the driving pulses with the relatively low levels.

What is claimed is:

1. A shock wave generating apparatus comprising:
   shock wave producing means constructed of at least two transducer elements, for producing shock wave pulses used to disintegrate an object located near a focal point of said shock wave producing means within a biological body under medical examination upon receipt of first drive pulses having first energy levels, and also for producing ultrasonic pulses used to obtain echo pulses reflected from said object near the focal point, as analog echo signals, upon receipt of second drive pulses having second energy levels lower than said first energy levels of said first drive pulses;
   analog type phase-shift correcting means for correcting phase shifts contained in said analog echo signals reflected from the object near the focal point by making respective phases of said analog echo signals coincident with each other as to a time domain of said analog echo signals, thereby obtaining an analog phase-corrected echo signal;
   peak detecting means for detecting a peak value of said analog phase-corrected echo signal; and
   controlling means for controlling said shock wave producing means based on said peak value of the analog phase-corrected echo signal to determine whether or not said shock wave pulses are produced in order to destroy the object near the focal point.

2. A shock wave generating apparatus as claimed in claim 1, wherein said analog type phase-shift correcting means comprises:
   envelope detectors for envelope-detecting said analog echo signals reflected from the object to obtain envelope-detected echo signals; and
   an adder for adding all of said envelope-detected echo signals to each other so as to make the respective phases of said envelope-detected echo signals coincident with each other with respect to said time domain.

3. A shock wave generating apparatus as claimed in claim 2, wherein each of said envelope detectors is arranged by an operational amplifier, a diode, and a buffer amplifier connected in a serial form.

4. A shock wave generating apparatus as claimed in claim 1, wherein said analog type phase-shift correcting means comprises:
   full-wave rectifiers for rectifying said analog echo signals reflected from the object in a full-wave rectification mode to obtain full-wave-rectified echo signals; and
   an adder for adding all of said full-wave rectified echo signals to each other so as to make the respective phases of said full-wave rectified echo signals coincident with each other in said time domain.

5. A shock wave generating apparatus as claimed in claim 1, wherein said analog type phase-shift correcting means comprises:
   half-wave rectifiers for rectifying said analog echo signals reflected from the object in a half-wave rectification mode to obtain half-wave-rectified echo signals; and
   an adder for adding all of said half-wave-rectified echo signals to each other so as to make the respective phases of said half-wave-rectified echo signals coincident with each other in said time domain.

6. A shock wave generating apparatus as claimed in claim 1, wherein said transducer elements of the shock wave producing means are arranged in a spherical form, as viewed in a sectional view.

7. A shock wave generating apparatus as claimed in claim 1, wherein said transducer elements of the shock wave producing means are ring-shaped elements.

8. A shock wave generating apparatus as claimed in claim 1, further comprising:
   transmitter delay means for giving predetermined delay times to said second drive pulses for said transducer elements; and
   receiver delay means for giving predetermined delay times to said analog echo signals reflected from the object near the focal point, whereby a focusing operation of said ultrasonic wave pulses by said shock wave producing means is electronically controlled.

9. A shock wave generating apparatus comprising:
   shock wave producing means constructed of at least two transducer elements, for producing shock wave pulses used to disintegrate an object located near a focal point of said shock wave producing means within a biological body under medical examination upon receipt of first drive pulses having first energy levels, and also for producing ultrasonic pulses used to obtain echo pulses reflected from said object near the focal point, as analog echo signals, upon receipt of second drive pulses having second energy levels lower than said first energy levels of the first drive pulses;

digital type phase-shift correcting means for correcting phase shifts contained in said analog echo signals reflected from the object near the focal point by converting said analog echo signals into digital echo signals, thereby obtaining digital phase-corrected echo signals with respect to a time domain of said echo signals;

peak detecting means for detecting peak values of said digital phase-corrected echo signals; and controlling means for controlling shock wave producing means based on said peak values of the digital phase-corrected echo signals so as to determine whether or not said shock wave pulses are produced in order to destroy the object near the focal point.

10. A shock wave generating apparatus as claimed in claim 9, wherein said digital type phase-shift correcting means comprises:

a multiplexer for sequentially receiving said analog echo signals and sequentially outputting said analog echo signals; and an A/D (analog-to-digital) converter for A/D-converting said analog echo signals into said digital echo signals.

11. A shock wave generating apparatus as claimed in claim 10, wherein said digital type phase-shift correcting means further includes:

a memory for storing said peak values of the digital echo signals; and an adder for adding all of said peak values of the digital echo signals so as to obtain said digital phase-corrected echo signals.

12. A shock wave generating apparatus as claimed in claim 9, wherein said peak detecting means comprises:

a comparator for sequentially comparing the peak values of said digital echo signals with each other to obtain higher peak values; and a register for temporarily storing said higher peak values obtained from the comparator.

13. A shock wave generating apparatus as claimed in claim 9, wherein said transducer elements of the shock wave producing means are arranged in a spherical form, as viewed in a sectional view.

14. A shock wave generating apparatus as claimed in claim 9, wherein said transducer elements of the shock wave producing means are ring-shaped elements.

15. A shock wave generating apparatus as claimed in claim 9, further comprising:

transmitter delay means for giving predetermined delay times to said second drive pulses for said transducer elements; and receiver delay means for giving predetermined delay times to said echo signals reflected from the object near the focal point, whereby a focusing operation of said ultrasonic wave pulses by said shock wave producing means is electronically controlled.

16. A shock wave generating apparatus comprising:

a shock wave pulse applicator constructed of at least two transducer elements, said shock wave pulse applicator producing shock wave pulses used to disintegrate an object located near a focal point of said shock wave pulse applicator within a biological body under medical examination upon receipt of first drive pulses having first energy levels, and also producing ultrasonic pulses used to obtain echo pulses reflected from said object near the focal point, as analog echo signals, upon receipt of second drive pulses having second energy levels lower than said first energy levels of said first drive pulses;

a phase-shift correcting circuit, said phase-shift correcting circuit correcting phase shifts contained in said analog echo signals reflected from the object near the focal point by making respective phases of said echo signals coincident with each other as to a time domain of said analog echo signals, thereby obtaining a phase-corrected echo signal;

a peak detector, said peak detector detecting a peak value of said phase-corrected echo signal; and a controller, said controller controlling said shock wave pulse applicator based on said peak value of the phase-corrected echo signal.

17. A shock wave generating apparatus as claimed in claim 16, wherein said phase-shift correcting circuit comprises:

envelope detectors for envelope-detecting said analog echo signals reflected from the object to obtain envelope-detected echo signals; and an adder for adding said envelope-detected echo signals to each other so as to make respective phases of said envelope-detected echo signals coincident with each other with respect to said time domain.

18. A shock wave generating apparatus as claimed in claim 17, wherein each of said envelope detectors comprises an operational amplifier, a diode, and a buffer amplifier connected in series.

19. A shock wave generating apparatus as claimed in claim 16, wherein said phase-shift correcting circuit comprises:

rectifiers for rectifying said analog echo signals reflected from the object to obtain rectified echo signals; and an adder for adding said rectified echo signals to each other so as to make the respective phases of said rectified echo signals coincident with each other in said time domain.

20. A shock wave generating apparatus as claimed in claim 16, wherein said phase-shift correcting circuit comprises:

a multiplexer for sequentially receiving said analog echo signals and sequentially outputting said analog echo signals;

an A/D (analog-to-digital) converter for A/D-converting said analog echo signals from said multiplexer into digital echo signals;

a comparator for sequentially comparing the peak values of said digital echo signals with each other to obtain higher peak values;

a memory for storing said peak values of the digital echo signals; and an adder for adding said peak values of the digital echo signals so as to obtain said phase-corrected echo signals.

* * * * *